United States Patent [19]

Takaya et al.

[11] Patent Number: 5,648,548

[45] Date of Patent: Jul. 15, 1997

[54] OPTICALLY ACTIVE ASYMMETRIC DIPHOSPHINE AND PROCESS FOR PRODUCING OPTICALLY ACTIVE SUBSTANCE IN ITS PRESENCE

[75] Inventors: Hidemasa Takaya, deceased, late of Shiga, by Miyoko Takaya, Chikako Takaya, Haruko Takaya, legal heirs; Tetsuo Ota, Kyoto; Koji Inagaki, Mie, all of Japan

[73] Assignee: Takasago International Corporation, Tokyo, Japan

[21] Appl. No.: 615,001

[22] Filed: Mar. 13, 1996

[30] Foreign Application Priority Data

Mar. 14, 1995 [JP] Japan .................... 7-080836

[51] Int. Cl.[6] .................................. C07F 9/02
[52] U.S. Cl. .................................. 568/17; 585/400
[58] Field of Search .................. 568/17; 585/400

[56] References Cited

U.S. PATENT DOCUMENTS

| | | | |
|---|---|---|---|
| 4,824,977 | 4/1989 | Devon et al. | 568/17 |
| 4,956,055 | 9/1990 | Packette | 568/17 |
| 5,508,438 | 4/1996 | Broger et al. | 568/17 |
| 5,510,503 | 4/1996 | Laue et al. | 568/17 |
| 5,530,150 | 6/1996 | Takaya et al. | 568/17 |

OTHER PUBLICATIONS

J. Am. Chem. Soc. 115, 7033–7034 (1993).

*Primary Examiner*—James H. Reamer
*Attorney, Agent, or Firm*—Sughrue, Mion, Zinn, Macpeak & Seas

[57] ABSTRACT

An optically active 2-diphenylphosphinomethyl-2'-diphenylphosphinyl-1,1'-binaphthalene derivative represented by the following general formula (I)

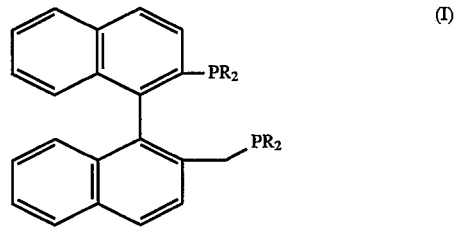

wherein R represents a phenyl group, a tolyl group, an anisyl group or a chlorophenyl group, and a process for the production of optically active substances in which the above compound and a transition metal compound are used. The asymmetric diphosphine of the present invention is related to the creation of novel compounds, which is excellent as a ligand for asymmetric synthesis use. When the above compound is used together with a transition metal compound such as of ruthenium, rhodium or the like, it shows markedly excellent properties as the catalyst of asymmetric hydrogenation and the like reactions, in terms of selectivity, conversion ratio, catalytic activity and the like.

3 Claims, No Drawings

OPTICALLY ACTIVE ASYMMETRIC DIPHOSPHINE AND PROCESS FOR PRODUCING OPTICALLY ACTIVE SUBSTANCE IN ITS PRESENCE

FIELD OF THE INVENTION

This invention relates to a novel optically active asymmetric diphosphine, more particularly to an asymmetric diphosphine (2-diphenylphosphinomethyl-2'-diphenylphosphinyl-1,1'-binaphthalene derivative) which is useful as a catalyst for various asymmetric synthesis reactions and to a process for the production of optically active substances in which the above compound and a transition metal compound are used.

BACKGROUND OF THE INVENTION

A large number of transition metal complexes are used as catalysts for organic synthesis reactions. Particularly, being stable and easy to handle, noble metal complexes have been used as catalysts in various synthesis studies in spite of their expensiveness, and many reports have been published stating that their use has rendered possible organic synthesis reactions which were not possible by conventional means. There are various types of optically active ligands to be used in such asymmetric catalysis reactions, including 2,2'-bis(diphenylphosphino)-1,1'-binaphthyl (to be referred to as "BINAP" hereinafter) ligand which is one of the catalysts having most excellent asymmetry recognizing ability. For example, Ru complexes having BINAP as a ligand show markedly excellent catalytic activity and enantio-selectivity for the asymmetric hydrogenation of olefins and ketones.

However, they are not so effective for the asymmetric hydrogenation reaction of relatively simple olefins having no heterofunctional groups in the substrate, and very little actually is known about catalyst systems which are effective for the asymmetric hydrogenation of such olefins.

Recently, an asymmetric ligand 2-(diphenylphosphino)-1,1'-binaphthalen-2'-yl) (1,1'-binaphthalen-2,2'-yl)phosphite (to be referred to as "BINAPHOS" hereinafter) having a binaphthyl nucleus but no C2 chirality has been reported by Sakai et al. (J. Am. Chem. Soc., vol.115, p.7033, 1993), which showed excellent performance in the asymmetric hydroformylation reaction of olefins.

However, such a compound having an optically pure binaphthyl nucleus has difficulty in effecting modification of functional groups in comparison with other compounds derived from optically pure tartaric acid or amino acids, and reports on the synthesis of its derivatives and asymmetric ligands are extremely scarce.

As described above, great effort has been directed toward the development of an asymmetric diphosphine ligand as a catalyst for asymmetric synthesis reactions, which shows a certain substrate selectivity, conversion ratio, catalytic activity, optical purity and the like that are different from those of the prior art BINAP derivatives. The present invention contemplates satisfying such demands.

It is accordingly an object of the present invention to provide a novel process for the asymmetric hydrogenation of optically active α-alkylstyrene derivatives, in which such an asymmetric diphosphine and a transition metal are used.

SUMMARY OF THE INVENTION

The inventors of the present invention have conducted intensive studies on ligands capable of showing catalytic functions in asymmetric synthesis reactions and found an asymmetric novel diphosphine ligand which has a binaphthyl nucleus but no C2 chirality. Further continued studies have resulted in the accomplishment of the present invention.

Accordingly, the gist of the present invention resides in:

(1) an optically active 2-diphenylphosphinomethyl-2'-diphenylphosphinyl-1,1'-binaphthalene derivative represented by the following general formula (I)

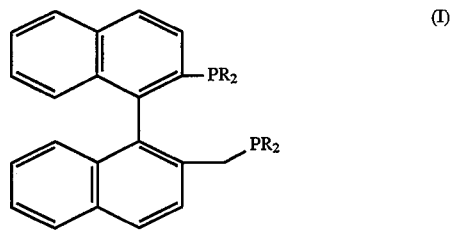

wherein R represents a phenyl group, a tolyl group, an anisyl group or a chlorophenyl group, (2) a process for producing optically active substances which comprises hydrogenating an α-alkylstyrene derivative in the presence of the binaphthalene derivative of the above item (1) and a transition metal compound, and (3) the process for producing optically active substances according to the above item (2) wherein the transition metal is ruthenium, rhodium, iridium or palladium.

Other objects and advantages of the present invention will be made apparent as the description progresses.

DETAILED DESCRIPTION OF THE INVENTION

Optically active substances and racemic bodies are present in the asymmetric diphosphine of the present invention represented by the general formula (I), and all of these optical isomers are included in the present invention.

The asymmetric diphosphine (I) of the present invention can be produced, for example, by a process shown by the following reaction scheme.

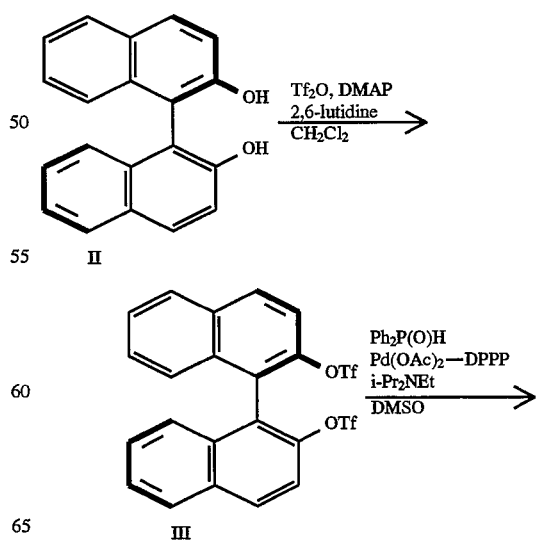

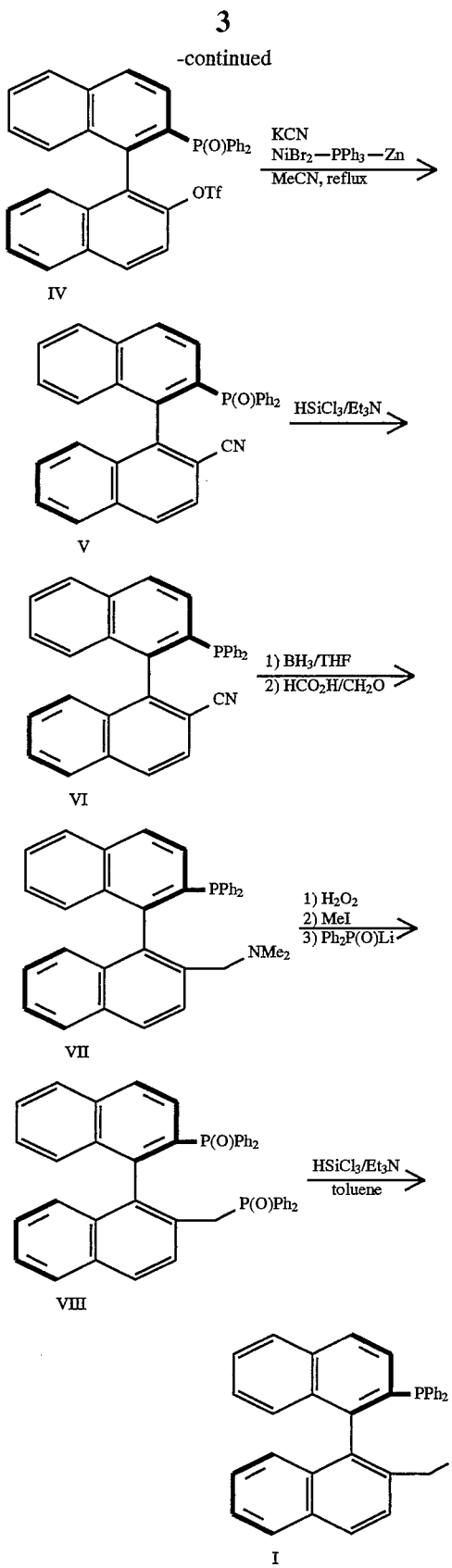

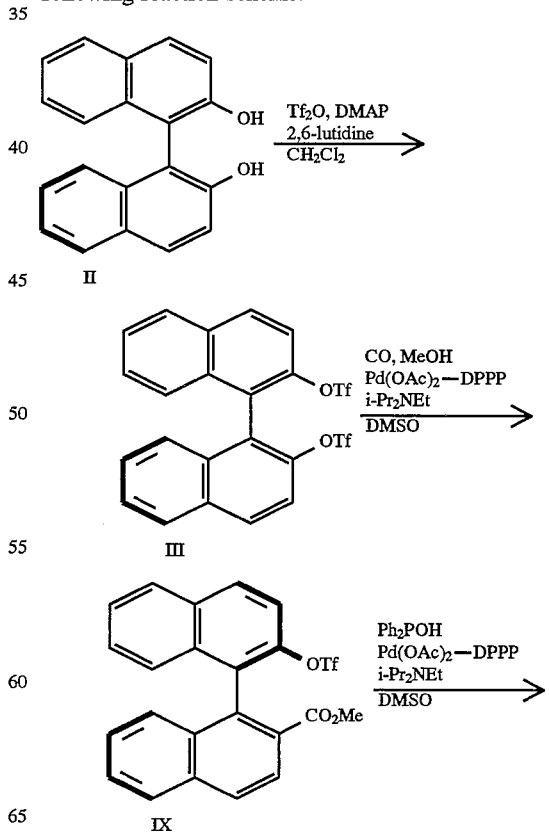

(III) is allowed to react with diphenylphosphine oxide in the presence of palladium acetate, 1,3-bisdiphenylphosphinopropane (DPPP) and N,N-diisopropylethylamine, thereby effecting monophosphinylation of the ditrifurate (III) to obtain a compound (IV). Next, the trifurate moiety of the compound (IV) is subjected to cyanogenation in the presence of a nickel catalyst to obtain a compound (V) almost quantitatively. The phosphine oxide moiety of the compound (V) is reduced with trichlorosilane in the presence of triethylamine to obtain a compound (VI) and then the cyano moiety of the compound (VI) is reduced using a borane-tetrahydrofuran complex to obtain an amine. When the thus obtained amine is subjected to methylation in the usual way (for example using formic acid and formaldehyde), a compound (VII) is obtained with a yield of 60%. The phosphine moiety of the thus obtained compound (VII) is oxidized with hydrogen peroxide, and the thus formed phosphine oxide is mixed with iodomethane and stirred in acetone to obtain the corresponding ammonium salt almost quantitatively. Next, the thus obtained ammonium salt and diphenylphosphinyllithium are heated under reflux in acetonitrile to obtain a coupling body diphosphine oxide (VIII) with a yield of 60%. Finally, the diphosphine oxide (VIII) is subjected to reduction in the usual way to produce the diphosphine compound (I) of interest with a high yield.

Alternatively, the asymmetric diphosphine (I) of the present invention may be produced in accordance with the following reaction scheme.

That is, an optically active binaphthol (II) is allowed to react with an anhydrous trifurate (Tf₂O) in the presence of 2,6-lutidine and 4-dimethylaminopyridine (DMAP), thereby obtaining a ditrifurate (III). The thus obtained ditrifurate

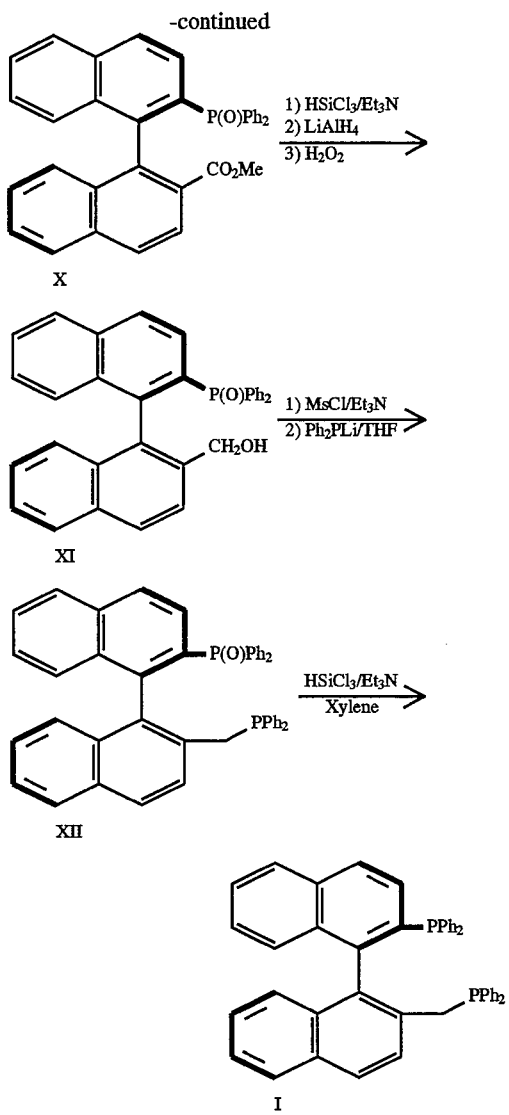

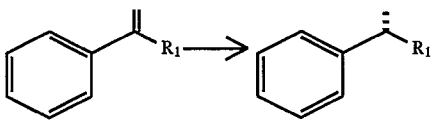

That is, the compound (III) is obtained in the same manner as described in the first reaction scheme and subjected to monomethoxycarbonylation using a palladium catalyst to obtain a compound (IX) with a yield of 71%. When diphenylphosphine oxide is introduced into the compound (IX), a compound (X) is obtained with a yield of 65%. Next, the phosphine oxide moiety of the compound (X) is reduced in the usual way, its carboxylic acid ester moiety is reduced and then the phosphine moiety is oxidized to obtain a compound (XI) from the compound (X) with a yield of 72%. When this is converted into mesylate and subjected to a coupling reaction with diphenylphosphinolithium, a compound (XII) is obtained, though its yield is small. In this connection, the inventors of the present invention have also tried its coupling reaction with diphenylphosphinyllithium, but the coupling product was hardly obtained, probably due to decrease in the nucleophilic property of the anion. Finally, the compound (XII) is subjected to reduction in the usual way to produce the diphosphine compound (I) of interest with a high yield.

The asymmetric diphosphine compound (I) of the present invention produced in this way can advantageously promote chemical reactions such as an asymmetric hydrogenation reaction and the like, when it is allowed to coexist in a reaction system with a transition metal compound prepared in advance. It can be used most suitably for the asymmetric hydrogenation reaction of olefinic unsaturated compounds having substituent groups, particularly α-alkylstyrene derivatives. It seems that partial or entire portions of the asymmetric diphosphine compound (I) and a transition metal compound form a complex in this reaction system.

Illustratively, when any one of the (R)-form and (S)-form of the diphosphine compound (I) is selected and allowed to coexist with a transition metal compound in a reaction system, an olefinic unsaturated compound in the reaction system is asymmetrically hydrogenated, so that its corresponding asymmetric hydrogenation product, namely an optically active substance having a desired absolute configuration, can be prepared at will.

For example, the asymmetric hydrogenation reaction of α-styrene is represented by the following formula:

wherein $R_1$ represents a $C_1$–$C_4$ lower alkyl group.

Examples of the transition metal to be used in the asymmetric hydrogenation reaction include ruthenium, rhodium, iridium or palladium and the like.

Illustrative examples of the transition metal compound include [Ru(benzene)Cl$_2$]$_2$, [Ru(benzene)Br$_2$]$_2$, [Ru(benzene)I$_2$]$_2$, [Ru(p-cymene)Cl$_2$]$_2$, [Ru(p-cymene)Br$_2$]$_2$, [Ru(p-cymene)I$_2$]$_2$, [(π-allyl)Ru(cod)]$_2$, [(π-methallyl)Ru(cod)]$_2$, [Rh(cod)Cl]$_2$, [Rh(cod)Br]$_2$, [Rh(nbd)Cl]$_2$, [Rh(nbd)Br]$_2$, [Rh(cod)$_2$]BF$_4$, [Rh(cod)$_2$]PF$_6$, [Rh(cod)$_2$]ClO$_4$, [Rh(nbd)$_2$]BF$_4$, [Rh(nbd)$_2$]PF$_6$, [Rh(nbd)$_2$]ClO$_4$, [Ir(cod)Cl]$_2$, [Ir(cod)Br]$_2$, [Ir(nbd)Cl]$_2$, [Ir(nbd)Br]$_2$, [Ir(cod)$_2$]BF$_4$, [Ir(cod)$_2$]PF$_6$, [Ir(cod)$_2$]ClO$_4$, [Ir(nbd)$_2$]BF$_4$, [Ir(nbd)$_2$]PF$_6$, [Ir(nbd)$_2$]ClO$_4$, Pd(OAc)$_2$, PdCl$_2$, PdCl$_2$(CH$_3$CN)$_2$, PdCl$_2$(PhCN)$_2$, Pd$_2$(dba)$_3$CHCl$_3$, [(π-allyl)PdCl]$_2$ and the like. In the above examples, the terms "cod", "nbd", and "dba" each represent "1,5-cyclooctadiene", "norbornadiene", and "dibenzylideneacetone", respectively.

With regard to the olefinic unsaturated compound as the reaction substrate, 2-phenyl-1-butene, 3,3'-dimethyl-2-phenyl-1-butene, 2-phenyl-1-pentene, 2-phenyl-1-hexene, α-cyclohexylstyrene, α-cyclopropylstyrene and the like can be used.

Examples of the solvent which can be used in the reaction include methanol, ethanol, isopropanol, benzene, toluene, ethyl acetate, tetrahydrofuran (to be referred to as "THF" hereinafter), methylene chloride, 1,2-dichloroethane, acetone and the like.

Amount of the asymmetric diphosphine compound (I) of the present invention to be used in the reaction may be in the range of from 0.1 to 10 mol %, preferably from 0.05 to 5 mol %, based on the aforementioned substrate. The transition metal compound may be used in an amount of from 0.05 to 20 mol %, preferably from 0.1 to 10 mol %, based on the substrate.

The reaction is carried out generally for 10 to 100 hours under a hydrogen pressure of from 1 to 100 atmospheres, preferably from 5 to 50 atmospheres, and at a temperature of from 10° to 100° C., preferably from 20° to 50° C., and these conditions are optionally adjusted depending on the amount of reactants and the like to be used.

EXAMPLES

Examples of the present invention are given below by way of illustration and not by way of limitation.

Equipments used herein for the measurement of various physical properties are as follows.

$^1$H NMR: JEOL JMN-EX-270 (270 MHz)
$^{13}$C NMR: JEOL JMN-EX-270 (67.5 MHz)
Polarimeter: DIP-360 (manufactured by JASCO)
GLC: GC-15A (Shimadzu Corp.)
MASS: QP-1000 (Shimadzu Corp.)

EXAMPLE 1

(a) Synthesis of (R)-2,2'-bis (trifluoromethanesulfonyloxy)-1,1'-binaphthalene (to be referred to as "trifurate" hereinafter) (III)

A 7.69 g (26.9 mmol) portion of (R)-binaphthol (II), 9.40 ml (80.7 mmol) of 2,6-lutidine and 1.32 g (10.8 mmol) of 4-dimethylaminopyridine were dissolved in 150 ml of methylene chloride and cooled to −40° C. To this was added dropwise 13.6 ml (80.8 mmol) of anhydrous trifurate, followed by 18 hours of stirring at room temperature. The solvent in the reaction mixture was evaporated under a reduced pressure, and the resulting residue was purified by a silica gel column chromatography (solvent: methylene chloride) to obtain 14.7 g (yield, 99%) of yellow crystals (ditrifurate) (III) having the following physical properties.
$^1$H NMR (CDCl$_3$) δ:7.25 (d, 2 H, J=8.3 Hz), 7.41 (ddd, 2 H, J=1.3, 6.9 and 8.3 Hz), 7.59 (ddd, 2 H, J=1.3, 6.9 and 8.3 Hz), 7.62 (d, 2 H, J=9.0 Hz), 8.01 (d, 2 H, J=8.3 Hz), 8.15 (d, 2 H, J=9.0 Hz)

(b) Synthesis of (R)-2-diphenylphosphinyl-2'-trifluoromethanesulfonyloxy-1,1'-binaphthalene (IV)

A mixture consisting of 1.37 g (2.49 mmol) of the ditrifurate (III) obtained in the above step (a), 1.06 g (5.26 mmol) of diphenylphosphine oxide, 256.5 mg (0.252 mmol) of Pd(OAc), 103 mg (0.250 mmol) of 1,3-bisdiphenylphosphinopropane, 1.9 ml (10.9 mmol) of N,N-diisopropylethylamine and 13 ml of dimethyl sulfoxide (to be referred to as "DMSO" hereinafter) was stirred for 14 hours at 90° C. in a stream of argon. The reaction mixture was mixed with saturated brine and extracted with diethyl ether. The extract was washed with 1 N HCl, saturated sodium bicarbonate aqueous solution and saturated brine and then dried on anhydrous magnesium sulfate. The resulting solution was concentrated under a reduced pressure and purified by a silica gel column chromatography (solvent: toluene-acetonitrile=9:1–3:1) to obtain 1.37 g (yield, 91%) of the title compound (IV) having the following physical properties.
$^1$H NMR (CDCl$_3$) δ:7.00 (d, 1 H, J=8.2 Hz), 7.14–7.52 (m, 15 H), 7.58 (ddd, 1 H, J=1.0, 6.9 and 7.9 Hz), 7.65 (dd, 1 H, J=11.5 and 8.6 Hz), 7.84 (d, 1 H, J=8.2 Hz), 7.90 (d, 1 H, J=8.9 Hz), 7.94 (d, 1 H, J=8.2 Hz), 8.01 (dd, 1 H, J=2.1 and 8.7 Hz)
$^{31}$P NMR (CDCl$_3$) δ:28.73 (s)

(c) Synthesis of (R)-2-diphenylphosphinyl-2'-cyano-1,1'-binaphthalene (V)

A flask was charged with 431 mg (0.143 mmol) of the dinaphthalene (IV) synthesized in the above step (b), 31.2 mg (0.143 mmol) of nickel bromide, 150 mg (0.573 mmol) of triphenylphosphine, 28.1 mg (0.430 mmol) of zinc powder and 55.9 mg (0.858 mmol) of potassium cyanate, and acetonitrile (3.0 ml) was added to the mixture in an atmosphere of argon gas. The thus prepared mixture was heated to its reflux temperature to carry out 84 hours of the reaction.

The blackish brown reaction mixture was cooled to room temperature, mixed with ethyl acetate and water, stirred and then allowed to stand to effect phase separation. The resulting oil layer was collected, washed twice with water and once with saturated sodium chloride aqueous solution and then dried on anhydrous magnesium sulfate. The resulting solution was concentrated under a reduced pressure, and the resulting crude product was purified by a silica gel column chromatography (developing solvent: ethyl acetate-hexane= 9:1–3:1) to obtain 340 mg (yield, 99%) of the title compound (V) having the following physical properties.
$^1$H NMR (CdCl$_3$) δ:7.02 (d, J=12.1 Hz, 1 H), 7.05 (d, J=12.1 Hz, 1 H), 7.15 –7.69 (m, 16 H), 7.84 (d, J=8.2 Hz, 1 H), 7.86 (d, J=8.6 Hz, 1 H), 7.96 (d, J=8.2 Hz, 1 H), 8.02 (dd, J=8.6 and 2.1 Hz, 1 H)
$^{31}$P NMR (CDCl$_3$) δ:28.35 (s)

(d) Synthesis of (R)-2-diphenylphosphino-2'-cyano-1,1'-binaphthalene (VI)

A 15 ml portion of toluene solution containing 333 mg (0.694 mmol) of the compound (V) synthesized in the above step (c) and 1.8 ml (13.9 mmol) of triethylamine was cooled to 0° C., and 0.7 ml (6.94 mmol) of trichlorosilane was added thereto. The thus prepared mixture was heated to its reflux temperature to carry out 60 hours of the reaction. The reaction mixture was cooled to room temperature, mixed with 1.0 ml of saturated sodium hydrogencarbonate aqueous solution and then stirred. The thus obtained suspension was filtered through celite, and the thus remained solid matter was washed with diethyl ether, dehydrated with magnesium sulfate and then concentrated under a reduced pressure. The resulting crude product was purified by a silica gel column chromatography (developing solvent: diethyl ether=9:1– 3:1) to obtain 298 mg (yield, 93%) of the title compound (VI) having the following physical properties. $^1$H NMR (CDCl$_3$) δ:6.96–7.33 (m, 14 H), 7.44–7.53 (m, 3 H), 7.75 (d, J=8.6 Hz, 1 H), 7.90–7.96 (m, 3 H), 8.02 (d, J=8.6 Hz, 1 H)
$^{31}$P NMR (CDCl$_3$) δ:−13.91 (s)

(e) Synthesis of (R)-2-diphenylphosphino-2'-dimethylaminomethyl-1,1'-binaphthalene (VII)

To 1.3 ml of a tetrahydrofuran solution containing 279 mg (0.601 mmol) of the above compound (VI) was added at 0° C. 1.3 ml of a tetrahydrofuran solution of 1.0 mol borane-tetrahydrofuran complex. This was heated to its reflux temperature to carry out 12 hours of the reaction. The reaction solution was concentrated under a reduced pressure, mixed carefully with 20 ml of 1 N hydrochloric acid aqueous solution and then heated to the reflux temperature. After 1 hour of reaction, the reaction mixture was cooled to room temperature and adjusted to a strongly alkaline pH (about 11) with 40% potassium hydroxide aqueous solution. This was mixed with ethyl acetate, stirred and then allowed to stand to effect phase separation. The resulting oil layer was collected, washed once with water and once with saturated sodium chloride aqueous solution and then dried by dehydration with anhydrous magnesium sulfate. The resulting solution was concentrated under a reduced pressure to obtain a crude product.

To the thus obtained crude product were added 0.68 ml (18.0 mmol) of formic acid and 0.68 ml (9.07 mmol) of 37% formaldehyde aqueous solution. After 35 hours of reaction at reflux temperature, the reaction solution was cooled to room temperature, mixed with 5 ml of saturated sodium hydrogencarbonate aqueous solution and then stirred. This was mixed with ethyl acetate, stirred and then allowed to stand to effect phase separation. The resulting oil layer was collected, washed once with water and once with saturated sodium chloride aqueous solution and then dried by dehydration with anhydrous magnesium sulfate. The resulting solution was concentrated under a reduced pressure to obtain a crude product which was subsequently purified by a silica gel column chromatography (developing solvent: ethyl acetate:hexane=9:1–3:1) to obtain 340 mg (yield, 99%) of the title compound (VII) having the following physical properties.

$^1$H NMR (CDCl$_3$) δ:1.92 (s, 6 H), 2.77 (d, J=14.2 Hz, 1 H) 3.05 (d, J=14.2 Hz, 1 H), 6.77–7.49 (m, 17 H), 7.84–7.99 (m, 17 H)

$^{31}$P NMR (CDCl$_3$) δ:–15.00 (s)

(f) Synthesis of (R)-2-diphenylphosphinylmethyl-2'-diphenylphosphinyl-1,1'-binaphthalene (VIII)

A 175 mg (0.354 mmol) portion of (R)-2-diphenylphosphinyl-2'-dimethylaminomethyl-1,1'-binaphthalene (VII) synthesized in the above step (e) was dissolved in 2 ml of chloroform, mixed with 2 ml of 6% hydrogen peroxide aqueous solution at room temperature and then stirred for 16 hours. The reaction mixture was extracted with chloroform and dried on anhydrous magnesium sulfate. The solvent was evaporated, and the thus obtained solid matter was dissolved in 2 ml of acetone, mixed with 0.2 ml (3.21 mmol) of methyl iodide and then stirred for 16 hours. When the solvent was evaporated under a reduced pressure, a light yellow solid matter was obtained. The ammonium salt obtained by adding 3 ml of acetonitrile was dissolved in 4 ml of diethyl ether and added to a solution of diphenylphosphinyllithium which has been prepared in advance from 59.4 mg (0.294 mmol) of diphenylphosphine oxide and 0.1 ml of n-butyllithium hexane solution (2.96 M). After 13 hours of heating under reflux, the reaction mixture was cooled to room temperature, mixed with 5 ml of 1 N hydrochloric acid to terminate the reaction and then extracted with ethyl acetate. The resulting organic layer was washed with saturated sodium bicarbonate aqueous solution and saturated brine and then dried on anhydrous magnesium sulfate. The resulting solution was concentrated under a reduced pressure and purified by a silica gel column chromatography (developing solvent: hexane-acetone=1:1–1:5) to obtain 111 mg (yield, 60%) of the title compound (VIII) having the following physical properties.

$^1$H NMR (CDCl$_3$) δ:2.57 (s, 2 H), 6.51–7.89 (m, 32 H)

$^{31}$P NMR (CDCl$_3$) δ:25.80 (s), 28.83 (s)

(g) Synthesis of (R)-2-diphenylphosphinomethyl-2'-diphenylphosphino-1,1'-binaphthalene (I) (R=phenyl group)

At 0° C., 1.8 ml (17.8 mmol) of trichlorosilane was added to a mixture consisting of 743 mg (1.11 mmol) of the compound (VIII) synthesized in the above step (f), 22 ml of toluene and 4.6 ml (35.5 mmol) of triethylamine, followed by 20 hours of heating under reflux. Thereafter, the reaction mixture was cooled to 0° C. and mixed with a small amount of saturated sodium bicarbonate aqueous solution to terminate the reaction. The suspension was filtered using celite and washed with ether. The organic layer was dried on anhydrous magnesium sulfate, and the resulting solution was concentrated under a reduced pressure and purified by a silica gel column chromatography (solvent: ether) to obtain 601 mg (yield, 85%) of the title compound (I) (R=phenyl group) having the following physical properties.

$^1$H NMR (CDCl$_3$) δ:2.94 (br d, 2 H, J=1.3 Hz), 6.66 (d, 1 H, J=8.3 Hz), 6.79 (ddd, 1 H, J=8.6, 6.9 and 1.7 Hz), 6.87–7.11 (m, 13 H), 7.16 –7.28 (m, 10 H), 7.33–7.42 (m, 3 H), 7.68–7.81 (m, 4 H)

$^{31}$P NMR (CDCl$_3$) δ:–15.19 (d, J=4.6 Hz), –14.24 (d, J=4.6 Hz)

EXAMPLE 2

(a) Synthesis of methyl (R)-1,1'-binaphthalene-2-trifluoromethanesulfonyloxy-2'-carboxylate (IX)

A 2.01 g (3.65 mmol) portion of ditrifurate (III) synthesized in the above step (a) of Example 1 was dissolved in 20 ml of DMSO to which were subsequently added 7.4 ml (183 mmol) of methanol and 1.4 ml (8.04 mmol) of N,N-diisopropylamine. The resulting solution was transferred into Schlenk tube which has been charged with 123 mg (0.55 mmol) of palladium acetate and 228 mg (0.55 mmol) of 1,3-bisdiphenylphosphinopropane and replaced with argon in advance, and the resulting mixture was stirred for 2 hours at 70° C. in an atmosphere of carbon monoxide. The reaction mixture was mixed with saturated brine and extracted with diethyl ether. The resulting extract was washed with 1 N hydrochloric acid and saturated sodium bicarbonate aqueous solution and then with saturated brine until the extract became neutral. The organic layer was dried on anhydrous magnesium sulfate, and the solution was concentrated under a reduced pressure and purified by a silica gel column chromatography (solvent: hexane-methylene chloride= 1:1–0:1) to obtain 1.19 g (yield, 71%) of white crystals of the title compound (IX) having the following physical properties.

$^1$H NMR (CDCl$_3$) δ:3.55 (s, 3 H), 7.14 (d, 1 H, J=7.3 Hz), 7.17 (d, 1 H, J=8.6 Hz), 7.33 (m, 2 H), 7.55 (m, 2 H), 7.57 (d, 1 H, J=8.9 Hz), 7.98 (d, 1 H, J=8.2 Hz), 7.99 (d, 1 H, J=8.2 Hz) 8.06 (d, 1 H, J=8.9 Hz), 8.08 (d, 1 H, J=8.6 Hz), 8.24 (d, 1 H, J=8.6 Hz)

(b) Synthesis of methyl (R)-1,1'-binaphthalene-2-diphenylphosphinyl-2'-carboxylate (X)

A 5.7 ml (32.7 mmol) portion of N,N-diisopropylamine was added to a mixture consisting of 3.44 g (7.47 mmol) of methyl (R)-1,1'-binaphthalene-2-trifluoromethanesulfonyloxy-2'-carboxylate (IX) synthesized in the above step (a), 3.03 g (15.0 mmol) of diphenylphosphine oxide, 48 ml of DMSO, 168 mg (0.747 mmol) of palladium acetate and 308 mg (0.747 mmol) of 1,3-bisdiphenylphosphinopropane, and the resulting mixture was stirred for 113 hours at 100° C. This was mixed with water and extracted with diethyl ether. The resulting extract was washed with 1 N hydrochloric acid and saturated sodium bicarbonate aqueous solution and then with saturated brine until the extract became neutral. The organic layer was dried on anhydrous magnesium sulfate, and the solution was concentrated under a reduced pressure and purified by a silica gel column chromatography (solvent: hexane-acetone=9:1–1:1) to obtain 2.30 g (yield, 60%) of the title compound (X) having the following physical properties.

$^1$H NMR (CDCl$_3$) δ:3.52 (s, 3 H), 6.97 (d, 1 H, J=8.2 Hz), 7.04–7.12 (m, 4 H), 7.17–7.27 (m, 3 H), 7.30–7.41 (m, 3 H), 7.45–7.55 (m, 4 H), 7.60 (d, 1 H, J=8.6 Hz), 7.65 (d, 1 H, J=8.6 Hz) 7.72 (d, 1 H, J=7.9 Hz), 7.77 (d, 1 H, J=8.6 Hz), 7.92 (d, 1 H, J=7.9 Hz), 7.94 (dd, 1 H, J=1.7 and 8.9 Hz)

$^{31}$P NMR (CDCl$_3$) δ:27.96 (s)

(c) Synthesis of (R)-2-diphenylphosphinyl-2'-hydroxymethyl-1,1'-binaphthalene (XI)

A solution consisting of 2.23 g (4.36 mmol) of methyl (R)-1,1'-binaphthalene-2-diphenylphosphinyl-2'- carboxylate (X) synthesized in the above step (b), 55 ml of xylene and 11.3 ml (87.3 mmol) of triethylamine was cooled to 0° C., mixed with 4.4 ml (43.6 mmol) of trichlorosilane and stirred at 120° C. for 16 hours. The reaction mixture was cooled to 0° C., mixed carefully with 35 ml of 35% sodium hydroxide aqueous solution and stirred for 20 minutes. This was further mixed with toluene to effect phase separation, and the resulting organic layer was dried on anhydrous magnesium sulfate. By evaporating the solvent, methyl (R)-1,1'-binaphthalene-2-diphenylphosphino-2'-carboxylate having the following physical properties was obtained.

$^1$H NMR (CDCl$_3$) δ:3.26 (s, 3 H), 6.97–7.29 (m, 14 H), 7.41–7.51 (m, 3 H), 7.88 (d, 2 H, J=8.3 Hz), 7.93 (d, 1 H, J=8.3 Hz), 8.02 (d, 1 H, J=8.6 Hz), 8.12 (d, 1 H, J=8.9 Hz)

$^{31}$P NMR (CDCl$_3$) δ:−14.69 (s)

The crude product was mixed with 500 mg (13.2 mmol) of lithiumaluminum hydride and 50 ml of THF and heated under reflux for 13 hours. The reaction mixture was cooled to room temperature, mixed with 0.5 ml of water, 0.5 ml of 3 N sodium hydroxide aqueous solution and 1.5 ml of water in that order and then filtered using celite. The thus obtained filtrate was dried on anhydrous magnesium sulfate, and the solvent was evaporated. The resulting residue was dissolved in 20 ml of chloroform, mixed with 15 ml of 6% hydrogen peroxide aqueous solution at room temperature and then stirred for 16 hours. After extraction with chloroform, the extract was dried on anhydrous magnesium sulfate, concentrated under a reduced pressure and then purified by a silica gel column chromatography (solvent: hexane-acetone= 5:1–1:1) to obtain 1.53 g (yield, 73%) of the title compound (XI) having the following physical properties.

$^1$H NMR (CDCl$_3$) δ:4.19 (d, 1 H, J=11.9 Hz), 4.36 (d, 1 H, J=11.9 Hz), 6.49 (d, 1 H, J=8.6 Hz), 6.71–6.94 (m, 4 H), 7.06–7.28 (m, 3 H), 7.44–7.57 (m, 7 H), 7.72–7.95 (m, 7 H)

$^{31}$P NMR (CDCl$_3$) δ:29.58 (s)

(d) Synthesis of (R)-2-diphenylphosphinomethyl-2'-diphenylphosphinyl-1,1'-binaphthalene (XII)

A 1.37 g (4.46 mmol) portion of (R)-2-diphenylphosphinyl-2'-hydroxymethyl-1,1'-binaphthalene (XI) synthesized in the above step (c) was dissolved in 11 ml of methylene chloride and cooled to −40° C. To this was added a solution prepared by dissolving 0.33 ml (4.26 mmol) of methanesulfonyl chloride in 2.8 ml of methylene chloride, followed by 20 minutes of stirring. After additional 30 minutes of stirring at room temperature, this was mixed with 1 N hydrochloric acid aqueous solution and extracted with chloroform. The extract was dried on anhydrous magnesium sulfate and concentrated under a reduced pressure to obtain a crude mesylate compound. This was dissolved in 5 ml of THF and added at 0° C. to diphenylphosphinous lithium which has been prepared in advance by heating 0.76 ml (4.23 mmol) of diphenylphosphinous chloride and 70 mg (10.1 mmol) of lithium in THF for 16 hours under reflux. After 17 hours of stirring at room temperature, the reaction mixture was extracted by adding water and benzene, and the resulting organic layer was dried on anhydrous magnesium sulfate. The resulting solution was concentrated under a reduced pressure and purified by a silica gel column chromatography (solvent: toluene-acetonitrile=9:1–3:1) to obtain 0.44 g (yield, 20%) of the title compound (XII) having the following physical properties.

$^1$H NMR (CDCl$_3$) δ:3.23 (dd, 1 H, J=14.5 and 1.8 Hz), 3.56 (dd, 1 H, J=14.5 and 1.8 Hz), 6.70–6.81 (m, 8 H), 6.91–7.54 (m, 15 H), 7.65–7.75 (m, 5 H), 7.86–7.95 (m, 4 H)

$^{31}$P NMR (CDCl$_3$) δ:−12.70 (s), 27.05 (s)

(e) Synthesis of (R)-2-diphenylphosphinomethyl-2'-diphenylphosphino-1,1'-binaphthalene (I) (R=phenyl group)

A solution consisting of 2.29 g (4.46 mmol) of (R)-2-diphenylphosphinomethyl-2'-diphenylphosphinyl-1,1'-binaphthalene (XII) synthesized in the above step (d), 50 ml of xylene and 11.5 ml (88.9 mmol) of triethylamine was cooled to 0° C., mixed with 6.8 ml (67.4 mmol) of trichlorosilane and then stirred at 120° C. for 21 hours. The reaction mixture was cooled to 0° C., mixed carefully with 50 ml of 35% sodium hydroxide aqueous solution and then stirred for 20 minutes. This was mixed with benzene to effect phase separation, and the resulting organic layer was dried on anhydrous magnesium sulfate. After evaporation of the solvent, the resulting residue was purified by a silica gel column chromatography (solvent: hexane-ethyl acetate= 9:1–4:1) to obtain 1.90 g (yield, 90%) of the compound (I) of interest (R=phenyl group).

EXAMPLE 3

Asymmetric hydrogenation of 2-phenyl-1-butene

A Schlenk tube was charged with 2.9 mg (0.006 mmol) of [Rh(cod)Cl]$_2$ and 9 mg (0.0141 mmol) of (R)-2-diphenylphosphinomethyl-2'-diphenylphosphino-1,1'-binaphthalene (I) (R=phenyl group) synthesized in Example 1, and the atmosphere in the tube was replaced by argon. The tube was further charged with 5 ml of methanol, 5 ml of benzene and 155 mg (1.17 mmol) of 2-phenyl-1-butene and transferred into a 50 ml capacity autoclave, and the thus prepared solution was stirred for 24 hours under a hydrogen pressure of 25 atmospheres and at a reaction temperature of 30° C. After completion of the reaction, the solvent was concentrated and then subjected to distillation using an air bath distiller to obtain 154 mg (yield, 98%) of the hydrogenated product.

The hydrogenated product showed an angle of rotation of [α]D −14.76° (cl. 0, 95% EtOH). This value shows that the compound has an optical purity of 65% e.e.

EXAMPLES 4 TO 6

Asymmetric hydrogenation of three substrates shown in Table 1 was carried out under the same reaction conditions as described in Example 3 except for the reaction time.

Angle of rotation of each of the thus hydrogenated products is shown in Table 1.

TABLE 1

| Example | R$_1$ in α-alkylstyrene | Reaction time (hr.) | Optical purity (% e.e.) |
|---------|------------------------|---------------------|------------------------|
| 4 | n-propyl | 58 | 77 |
| 5 | n-butyl | 24 | 55 |
| 6 | t-butyl | 27 | 33 |

Thus, it is evident that the novel asymmetric diphosphine of the present invention is markedly excellent as a ligand for asymmetric synthesis use and, when used together with a transition metal compound such as of ruthenium, rhodium or the like, shows excellent properties as the catalyst of asymmetric hydrogenation and the like reactions, in terms of selectivity, conversion ratio, catalytic activity and the like.

While the invention has been described in detail and with reference to specific embodiments thereof, it will be apparent to one skilled in the art that various changes and modifications can be made therein without departing from the spirit and scope thereof.

What is claimed is:

1. An optically active 2-diphenylphosphinomethyl-2'-diphenylphosphinyl-1,1'-binaphthalene derivative represented by the following general formula (I)

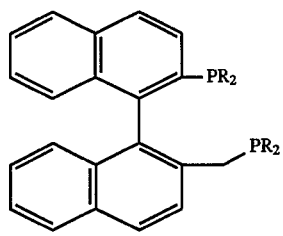

(I)

wherein R represents a phenyl group, a tolyl group, an anisyl group or a chlorophenyl group.

2. A process for producing optically active substances which comprises hydrogenating an α-alkylstyrene derivative in the presence of an optically active 2-diphenylphosphinomethyl-2'-diphenylphosphinyl-1,1'-binaphthalene derivative represented by the following general formula (I):

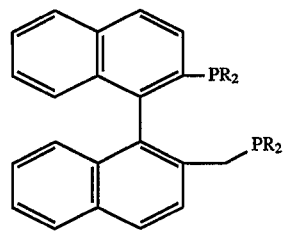

(I)

wherein R represents a phenyl group, a tolyl group, an anisyl group or a chlorophenyl group, and a transition metal compound.

3. The process for producing optically active substances according to claim 2, wherein said transition metal is ruthenium, rhodium, iridium or palladium.

* * * * *